United States Patent [19]

Difilippantonio et al.

[11] Patent Number: 5,582,603
[45] Date of Patent: Dec. 10, 1996

[54] MULTIPLE SLIVER ABSORBENT PRODUCT

[75] Inventors: Michelle L. Difilippantonio, Edison; Winifred C. Dabroski, East Brunswick, both of N.J.

[73] Assignee: McNeil-PPC, Inc., Skillman, N.J.

[21] Appl. No.: 401,334

[22] Filed: Mar. 9, 1995

Related U.S. Application Data

[63] Continuation of Ser. No. 915,778, Jul. 16, 1992, abandoned, which is a continuation of Ser. No. 852,936, Mar. 13, 1992, abandoned, which is a continuation of Ser. No. 701,298, May 13, 1991, abandoned, which is a continuation of Ser. No. 581,176, Sep. 6, 1990, abandoned, which is a continuation of Ser. No. 313,933, Feb. 22, 1989, abandoned.

[51] Int. Cl.$^6$ .......................... A61F 13/15; A61F 13/20
[52] U.S. Cl. ............... 604/380; 604/378; 604/385.1; 604/359
[58] Field of Search .................. 604/358–360, 604/378–380, 381–382, 385.1

[56] References Cited

U.S. PATENT DOCUMENTS

| | | | |
|---|---|---|---|
| 2,890,700 | 6/1959 | Lönberg-Holm | 604/380 X |
| 2,952,259 | 9/1960 | Burgeni | 604/380 X |
| 3,371,667 | 3/1968 | Morse | 604/369 |
| 3,995,636 | 12/1976 | Murray et al. | 604/359 X |
| 4,213,459 | 7/1980 | Sigl et al. | 604/380 |
| 4,223,677 | 9/1980 | Anderson | 604/378 |
| 4,333,463 | 6/1982 | Holtman | 604/368 |
| 4,501,586 | 2/1985 | Holtman | 604/380 |
| 4,723,954 | 2/1988 | Pieniak | 604/384 |
| 4,842,593 | 6/1989 | Jordan et al. | 604/360 |
| 4,872,870 | 10/1989 | Jackson | 604/366 |
| 5,037,412 | 8/1991 | Tanzer et al. | 604/359 |
| 5,188,624 | 2/1993 | Young, Sr. et al. | 604/378 |

FOREIGN PATENT DOCUMENTS

| | | | |
|---|---|---|---|
| 2131699 | 6/1984 | United Kingdom | 604/358 |
| 2131700 | 6/1984 | United Kingdom | 604/358 |
| 2165757 | 4/1986 | United Kingdom | 604/358 |
| 2254255 | 10/1992 | United Kingdom | 604/378 |

*Primary Examiner*—John G. Weiss
*Assistant Examiner*—P. Zuttarelli

[57] ABSTRACT

This invention relates to an improved multiple sliver absorbent product having a bottom sliver with low density edges. The low density edges engage a low density upper sliver and provide traction between the slivers which aids in stabilizing the product.

14 Claims, 2 Drawing Sheets

MULTIPLE SLIVER ABSORBENT PRODUCT

This is a continuation of application Ser. No. 07/915,778, filed Jul. 16, 1992; now abandoned; which was a continuation of application Ser. No. 07/852,936, filed Mar. 13, 1992; now abandoned; which was a continuation of application Ser. No. 07/701,298 filed May 13, 1991; now abandoned; which was a continuation of application Ser. No. 07/581,176 filed Sep. 6, 1990; now abandoned; which was a continuation of application Ser. No. 07/313,933 filed Feb. 22, 1989; now abandoned.

FIELD OF THE INVENTION

This invention relates to protective absorbent products for use in undergarments, having more than one absorbent batt or sliver. More particularly, this invention relates to sanitary protection products having improved stability and absorbency.

BACKGROUND OF THE INVENTION

Sanitary napkins and other absorbent products have customarily included a central absorbent element having a body-facing side, a garment-facing side, longitudinally extending edges and transverse ends. The central absorbent element is usually composed of an absorbent batt or sliver containing hydrophilic fibers. Some multiple-silver absorbent products are known to have been made commercially available as sanitary napkins. Such sanitary napkins have more than one absorbent batt layer, or sliver, to provide additional absorbent volume for absorbing body fluid. In addition, dual-sliver absorbent products have been known to be used for the purpose of stabilizing the absorbent product in providing resiliency during wear. In such cases, a bottom, undergarment-facing sliver can be compressed to raise its density higher than that of a top, body-facing sliver. In such a construction, the bottom sliver serves to provide a reservoir layer of high density absorbent batt in which fluid may be trapped. The lower density upper sliver quickly wicks fluid into the pad. It also provides a stable, crush-resistant absorbent pad which resists roping and twisting during use.

However, in such constructions, due to the varying density between the top and bottom slivers, the slivers tend to slip and slide against one another and become unstable, despite their intended purpose. Although adhesives can be used to stabilize such a design, using adhesives in such an absorbent product is expensive and difficult to carry out. For example, in production, the dust from pulp slivers tends to clog adhesive application nozzles. Where water-based adhesive is used, the moisture level of the napkin increases and provides a breeding ground for mold and other growths. In use, adhesive may interfere with the absorbency of the napkin.

It is, therefore, an object of this invention to provide a stable multiple-sliver absorbent product which does not require adhesive to preserve its integrity.

Yet another object of this invention is to provide a stable dual sliver absorbent product which may be used as a sanitary napkin device.

Yet another object of this invention is to provide a comfortable, stable sanitary protection device which has the advantages of a high density lower sliver and low density upper sliver and yet does not twist or deform or come apart in use.

Other objects of this invention will become apparent through the ensuing description.

SUMMARY OF THE INVENTION

This invention relates to a multiple sliver absorbent product having at least two layers of absorbent batt, a lower, undergarment-facing layer which varies in density transversely from longitudinal edge to edge. The central portion of the lower layer is compressed to increase its density. An upper body-facing absorbent batt layer has relatively lower density than the central portion of the lower layer. More particularly, the lower sliver of the absorbent product of this invention has two longitudinal edges and two transverse edges. The longitudinal edges of the sliver have relatively low density and remain "fluffy" in appearance. The central portion of the lower sliver is compressed and has a relatively higher density than the edges and the upper sliver. When the lower and upper slivers are placed in proximity to one another, the fluffy edges of the lower sliver engage the low density upper sliver. The fibers of the longitudinal edges of the lower sliver and those of the upper sliver entangle and provide an interaction which improves the stability of the absorbent product.

Thus, the absorbent products of this invention provide the advantages of a higher density lower sliver with the stability of a single sliver absorbent pad. The lower and upper slivers tend to remain in tandem and do not slide away from one another in use. The fluffy edges of the bottom sliver provide greater comfort than if they were sharp and hard and highly dense as is the remainder of the bottom sliver.

DETAILED DESCRIPTION OF PREFERRED EMBODIMENTS

Figure 1:
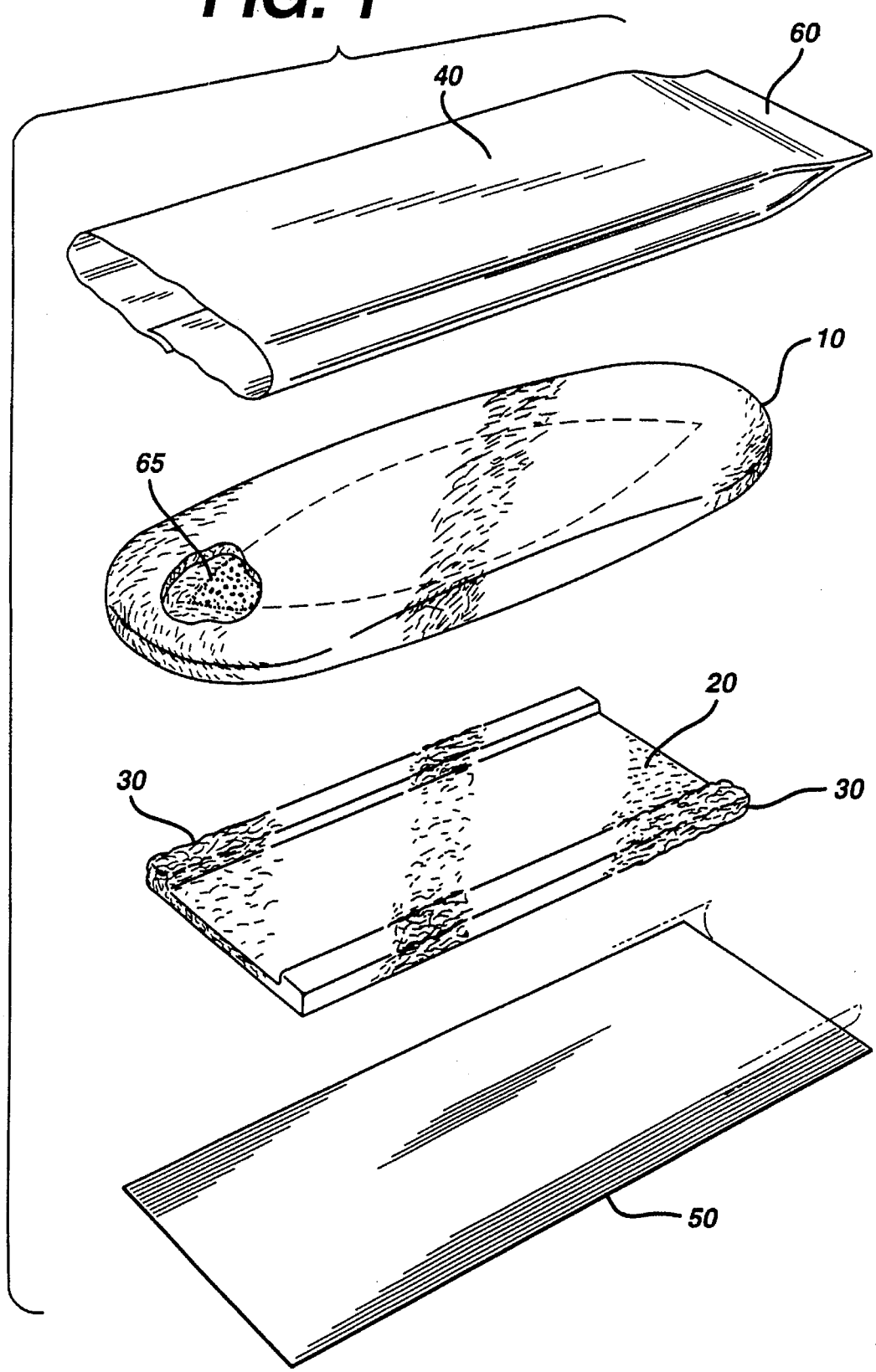
FIG. 1 is an exploded view of the preferred embodiment of the napkin.

In accordance with the teachings of this invention, an absorbent product containing at least two absorbent slivers is provided. One preferred embodiment of the product of this invention is a sanitary napkin, which includes a central absorbent element having a lower sliver with low density longitudinal edges and a higher density center portion, and an upper sliver of relatively low density. The sanitary napkin products of this invention should have a fluid pervious cover on its body-facing side and a fluid impermeable barrier on its undergarment-facing side.

Preferably, the sanitary napkins of this invention should be between about 4 and about 10 inches in length, more preferably, about 6 and about 9 inches. The upper sliver is preferably as long as the sanitary napkin. The lower sliver is preferably smaller than the upper sliver. The lower sliver is preferably between about 3 and about 9 inches in length, more preferably, between about 5 and about 7 inches. The surface area of the lower sliver should be between about 30 and about 90% of that of the upper sliver. More preferably, it should be between about 50 and about 75% of the area.

The absorbent slivers of this invention are preferably made of loosely associated absorbent hydrophilic materials such as cellulose fibers, wood pulp, regenerated cellulose of cotton fiber, and/or other materials generally known in the art. Such fibers may be chemically or physically modified and the core may include such fibers in combination with other materials, both natural and synthetic, including other fibers, foams, polymers, and the like. However, for the preferred embodiment of this invention, wood pulp is the material of choice because of its availability and inexpensive cost. The bottom sliver may contain superabsorbents to increase its fluid capacity, or thermoplastic fibers which, when heated, can improve adherence to the upper sliver.

The body fluid pervious cover which surrounds the side of the napkin to be worn against the body of the user can be a resilient, relatively non-absorbing, fluid pervious material. This material is provided for comfort and conformability and directs fluid to the underlying absorbent core, for example, wood pulp, which retains such fluid. This cover may be any woven or nonwoven material pervious to body fluid contacting its surface, and should be soft and easily permeated by body fluids. Preferably, the cover should be made of a material which allows the passage of fluid without wicking it appreciably in its horizontal plane. Furthermore, it should retain little or no fluid in its structure to provide a relatively dry surface next to the skin. Generally, the cover is a single, rectangular sheet of material having a width sufficient to cover the body-facing side of the central absorbent element. Preferably, the cover is longer than the central absorbent element so as to form end tabs, which may be sealed with another pervious or impervious layer to fully enclose the central absorbent element. The cover need not be fully wrapped around the entire product, but may be sealed to the barrier at the product's sides and ends. The cover may be sealed adhesively, mechanically or thermally. The cover is preferably made of hydrophilic or hydrophobic fibers or filaments or films of thermoplastic hydrophobic polymers such as polyethylene or polypropylene. Fibrous covers may be bonded with emulsions including acetate acrylics, styrenes, vinyls, urethanes or the like. Fibrous covers may be composed of rayon, polyester, nylon, polyethylene fibers or the like. Preferably, the cover is an apertured fibrous polyester cover.

The sanitary napkins of this invention should also include a body fluid impermeable barrier on the undergarment-facing side of the central absorbent element. The barrier may be moisture-vapor permeable to allow passage of air and moisture vapor while substantially blocking the passage of liquids to the outer surface. The barrier may be heat sealed or fastened by way of adhesives to the central absorbent element. The barrier may be made up of any thin, flexible, body-fluid impermeable material such as a polymeric film of, for example, polyethylene, polypropylene, or cellophane, glassine or even a normally fluid pervious material that has been treated to be impervious such as impregnated or coated repellant paper or nonwoven fabric.

The densification and processing of the varying-density bottom sliver can be achieved using a calendar roll or similar device, such as an embossing roll. The bottom sliver may also be densified by stamping it with a rectangular plate or by subjecting it to a vacuum. A heated calendar roll may be used, or, the sliver may be wetted or subjected to pressure. The pulp is calendared through a central absorbent section and the longitudinal edges are allowed to remain less dense. Of course, the edge density may be varied using pressure from a calendar roll as well. The edges of the roll may be gnurled and its central portion, smooth, in order to achieve the desired density variations. However, the lower the edge density, the greater the ability of the bottom and top slivers to adhere to one another. The density of the top sliver should be between about 0.1 and 1.0 g/in$^3$, more preferably between about 0.4 and about 0.6 g/in$^3$. The central portion of the bottom sliver should be between about 0.5 and about 2 g/in$^3$, more preferably about 1.0 to about 1.5 g/in$^3$.

Table I illustrates the relationship between edge density and adherence. Four samples of absorbent product of this invention were produced, each having a center density of 1.05 grams per cubic inch. The edge density was varied from 0.23 to 0.38 grams per cubic inch. The adherence of the bottom sliver to the top sliver was tested by pulling the bottom sliver across the top sliver and noting the force required to move the bottom sliver. As indicated in Table I, a force of 20 grams was needed to pull the uniform density sliver while a force of 85 grams was required to pull a sliver having a center density of 1.05 grams per cubic inch and an edge density of 0.23 grams per cubic inch. Preferably, the fluffy edge of the bottom sliver is sufficiently wide on each longitudinal edge to provide a area for traction between the upper and lower slivers. Thus, each longitudinal edge of low density should be between about ⅛ to about ⅞ inch in width. The edge density should be between about 0.25 and 0.5 g/in$^3$, more preferably between about 0.25 and 0.38 g/in$^3$. A substantial portion of the central absorbent area should be densified, and this can vary from about ½ inch to about 2 inches, depending upon the size of the bottom sliver.

The absorbent products of this invention may contain more than one lower sliver having "fluffy" edges. In this way, several slivers may be stacked and engage each other's edges while maintaining the stability of the pad. Likewise, more than one low density top sliver may be used.

Figure 2:
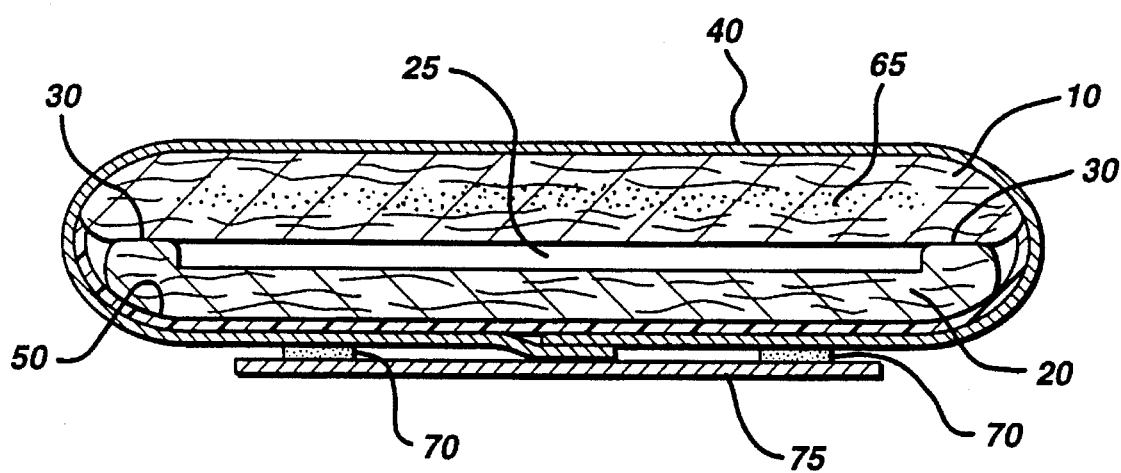
FIG. 2 is a cross sectional of the preferred embodiment of the napkin shown in the exploded view of FIG. 1.

FIGS. 1 and 2 depict a preferred embodiment of the products of this invention. The absorbent pad depicted in FIG. 1 is an exploded view of a sanitary napkin having a top sliver 10 and a bottom sliver 20. FIG. 2 is a cross-section of this sanitary napkin. The longitudinal

TABLE I

| Sample | Center Density (g/in$^3$) | Edge Density (g/in$^3$) | Force (g) |
| --- | --- | --- | --- |
| 1 | 1.05 | 1.05 | 20 |
| 2 | 1.05 | 0.38 | 70 |
| 3 | 1.05 | 0.32 | 80 |
| 4 | 1.05 | 0.23 | 85 | edges 30 of the bottom sliver 20 are raised and are of lower density than the remainder of bottom sliver 20. Compressed central portion 25 preferably extends along the length of the napkin, although it may be only in the center, surrounded peripherally by the lower density edge. These edges 30 engage the top sliver 10 just inward of the longitudinal edges of top sliver 10. The entire construction is wrapped with a fluid-permeable cover 40. A fluid-impermeable barrier layer 50 may be placed beneath the bottom sliver 20 in order to prevent body fluid from contacting the undergarment on which it is worn. In FIGS. 1 and 2, the cover 40 is wrapped entirely around the construction including the impermeable barrier 50. However, barrier 50 may be wrapped over the cover layer beneath the bottom sliver. Preferably, overwrap cover 40 is sealed at the transverse ends of the product so as to form a flange 60. Positioning adhesive 75 may be placed along the length of the napkin on the undergarment-facing side. This may be a pressure-sensitive adhesive or the like. A protective release strip made of coated paper, as known to those of ordinary skill in the art, may be used to cover the adhesive until use.

Preferably, the transverse ends of the top sliver have been tapered rather than being of a depth uniform with that of the remainder of the top sliver. This provides additional comfort for the wearer in use.

Preferably, the fluid permeable cover contains a binder (i.e., acrylic compound) which can adhere to the top of the upper sliver upon heating. This improves the cover's fluid permeability and aids in drawing the fluid through the cover and into the pad.

In another preferred embodiment of the products of this invention, the top sliver 10 includes a layer of powdered deodorant ingredient, including bicarbonate of soda, microencapsulated fragrance, or the like. Referring to FIG. 1, the odor control agent 65 may be placed in top sliver 10. Such odor control ingredients may be active or passive. Passive fragrance materials may be used to mask the odor of menstrual fluid or other body fluids. Active odor control ingredients, e.g., sodium bicarbonate and the like, may be used to interact with the odors of the body fluid to provide active odor control.

Such odor control ingredients may be sprayed or sprinkled into the top sliver during the formation of the top sliver, or they may be placed on a matrix which is placed within or below the top sliver while it is being formed. Preferably, an efficacious amount of the odor control agent is placed in the upper sliver of the pad and extends substantially along the length of the pad. The odor control agent should be no closer to the body-facing surface of the pad than about 0.10 inch, and no further away than about 0.5 inch, more preferably, 0.35 inch. Most preferably, it should be no further away than about 0.25 to about 0.35 inch. Preferably, the odor control agent 65 is distributed along the longitudinal axis of the top sliver 10 in an elliptical patterns as shown in FIG. 1, such that a majority of the agent is located in the central portion of the top sliver 10. Preferably, the odor control agent in sodium bicarbonate. Between about 5 mg—1 g of sodium bicarbonate may be used, more preferably about 50 mg to about 400 mg.

In another preferred embodiment, a top sliver is vacuum-formed. Its length is about 8 inches and its width is about 2.5 inches. It is composed of 100% wood pulp fluff. A second, bottom sliver is vacuum-formed and is approximately 6 inches in length and 2 inches in width. The top sliver is about 0.65 inch in depth. The bottom sliver is calendared using a calendar roll to a thickness of about 0.065 inch in the central portion. The edges are allowed to remain uncalendared to a width of about 0.5 inch. The two slivers are then brought together and covered with an apertured fibrous cover fabric made of polyester and containing a bonding agent which is heat-activated. During the vacuum-forming of the top sliver, about 250 mg of sodium bicarbonate is sprayed along the length of the sliver about 0.25 inch from the top surface such that the highest concentration of sodium bicarbonate is toward the center of the sliver. A polypropylene repellant barrier is applied to the bottom of the bottom sliver. The product is subjected to heat and pressure to adhere the cover to the top sliver. The ends of the cover are sealed in flanges and positioning adhesive applied in strips to the bottom of the product along the longitudinal axis. A release paper strip is applied to the pressure-sensitive positioning adhesive to protect it prior to use. This product is able to absorb body fluid when applied to the undergarment of a wearer.

It should be noted that, although FIG. 2 depicts a gap between top sliver 10 and bottom sliver 20 this gap is exaggerated and, in use, the pulp or other absorbent medium of top sliver 10 fills in this gap.

The pulp slivers may be vacuum-formed, air-laid, die-cut, or otherwise made according to processes known to those of ordinary skill in the art. The bottom sliver is then calendared in its central area and brought into contact with the top sliver. The bottom and top slivers may then be compressed so as to cause the fluffy edges of the bottom sliver to engage the top sliver. The bottom portion of the product is then wrapped in an impermeable barrier such as lower polyolefin (i.e. polyethylene or polypropylene). The entire construction is then wrapped in a permeable cover, which may be made of cellulose, rayon, an apertured fiber, entangled cover or an apertured hydrophobic cover. The cover is then sealed at its transverse ends, although it may be wrapped or otherwise provided with closure and adhered below the bottom sliver and barrier layers with adhesive. A pressure sensitive adhesive 70 is then applied to the bottom of the cover in order to provide means for affixing such product to the undergarment of the wearer. The adhesive 70 is covered with a release paper 75 prior to use.

Of course, the absorbent product of this invention may be made into a diaper, incontinence product, or wound dressing or the like. It provides a stable construction for absorbing body fluid which is comfortable and provides excellent absorption capacity.

What is claimed is:

1. An absorbent product for absorbing body fluid comprising:

a) a central absorbent core comprising a fibrous lower sliver and a fibrous top sliver, said lower sliver having a densified central portion, transverse ends and longitudinal edges, the longitudinal edges having a density lower than that of the densified central portion, and said top sliver having a density lower than that of the densified central portion of the lower sliver, such that the fibers of the longitudinal edges of the lower sliver and the fibers of the top sliver engage to prevent slippage between the slivers;

b) a fluid permeable cover; and c) a fluid impermeable barrier.

2. A product according to claim 1 wherein said top sliver contains an efficacious amount of active odor control agent.

3. A product according to claim 2 wherein said active odor control agent is sodium bicarbonate.

4. A product according to claim 3 wherein said top sliver contains about 5 mg to about 1 g of sodium bicarbonate.

5. A product according to claim 2 wherein said active odor control agent is a powder disposed in an elliptical pattern within the top sliver.

6. A product according to claim 1 wherein the transverse ends of said top sliver are tapered.

7. A product according to claim 1 wherein said top sliver has a surface area and said lower sliver has a surface area and wherein the surface area of said lower sliver is between about 30 and 90% of the surface area of the top sliver.

8. A product according to claim 1 wherein the longitudinal edges of the bottom sliver have a density between about 0.25 and about 0.5 g/in$^3$.

9. A product according to claim 8 wherein the density of the top sliver is between about 0.4 and about 0.6 g/in$^3$.

10. A product according to claim 8 wherein the density of the central portion of said bottom sliver is from about 0.5 and about 2 g/in$^3$.

11. A product according to claim 1 wherein the absorbent product is a sanitary napkin.

12. A product according to claim 1 wherein the absorbent product is a wound dressing.

13. A product according to claim 1 wherein the absorbent product is an incontinence device.

14. A product according to claim 1 wherein the absorbent product is a diaper.

* * * * *